(12) United States Patent
Sun et al.

(10) Patent No.: US 11,647,959 B2
(45) Date of Patent: May 16, 2023

(54) SAMPLING DEVICE FOR DRUG DEVELOPMENT AND DIAGNOSIS OF GASTRIC-INTESTINAL DISEASES

(71) Applicant: THE REGENTS OF THE UNIVERSITY OF MICHIGAN, Ann Arbor, MI (US)

(72) Inventors: Duxin Sun, Ann Arbor, MI (US); Yogesh B. Gianchandani, Ann Arbor, MI (US); Tao Li, Ann Arbor, MI (US); Jinhui Liao, Ann Arbor, MI (US); Qisen Cheng, Ann Arbor, MI (US); Johnathan Lewis, Ann Arbor, MI (US); Ryan Meredith, Ann Arbor, MI (US); Jeremy Felton, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 211 days.

(21) Appl. No.: 16/958,165

(22) PCT Filed: Jan. 2, 2019

(86) PCT No.: PCT/US2019/012073
§ 371 (c)(1),
(2) Date: Jun. 26, 2020

(87) PCT Pub. No.: WO2019/136081
PCT Pub. Date: Jul. 11, 2019

(65) Prior Publication Data
US 2020/0367828 A1 Nov. 26, 2020

Related U.S. Application Data

(60) Provisional application No. 62/612,834, filed on Jan. 2, 2018.

(51) Int. Cl.
*A61B 5/145* (2006.01)
*A61B 10/00* (2006.01)
(Continued)

(52) U.S. Cl.
CPC .............. *A61B 5/6861* (2013.01); *A61B 5/01* (2013.01); *A61B 5/036* (2013.01); *A61B 5/073* (2013.01);
(Continued)

(58) Field of Classification Search
CPC .............. A61B 5/6861; A61B 10/0045; A61B 10/0061; A61B 2562/162
See application file for complete search history.

(56) References Cited

U.S. PATENT DOCUMENTS

2005/0154277 A1 7/2005 Tang et al.
2005/0272972 A1* 12/2005 Iddan .................... A61B 1/041
600/102

(Continued)

FOREIGN PATENT DOCUMENTS

CN 201719266 U 1/2011

OTHER PUBLICATIONS

International Search Report and Written Opinion of the International Searching Authority issued in PCT/US2019/012073, dated Apr. 23, 2019; ISA/KR.

*Primary Examiner* — Eric F Winakur
(74) *Attorney, Agent, or Firm* — Harness, Dickey & Pierce, P.L.C.

(57) ABSTRACT

An ingestible electronic capsule for the collection of samples along a gastric intestinal tract and methods relating thereto are provided. The ingestible electronic capsule includes a housing and a cap that form an interior chamber. The cap includes a sampling port and one or more sample collection chambers are disposed within the interior cham- (Continued)

ber. A motor is also disposed within the interior chamber and is configured to rotate one of the cap and the one or more sample collection chambers so to align one or the one or more sample collection chambers and the sampling port of the cap so to allow for sample collection. A microcontroller is also disposed within the interior chamber and is in communication with at least the motor. The microcontroller is configured to control the selective alignment of the sampling port and one of the one or more sample collection chambers and induce gastric intestinal fluid sampling.

18 Claims, 8 Drawing Sheets

(51) Int. Cl.
*A61B 5/01* (2006.01)
*A61B 5/03* (2006.01)
*A61B 5/00* (2006.01)
*A61B 5/07* (2006.01)

(52) U.S. Cl.
CPC ...... *A61B 5/14539* (2013.01); *A61B 10/0045* (2013.01); *A61B 5/4255* (2013.01); *A61B 2010/0061* (2013.01); *A61B 2560/0214* (2013.01); *A61B 2562/06* (2013.01); *A61B 2562/162* (2013.01)

(56) References Cited

U.S. PATENT DOCUMENTS

| | | |
|---|---|---|
| 2007/0100200 A1 | 5/2007 | Suzuki et al. |
| 2015/0011874 A1 | 1/2015 | Amoako-Tuffour et al. |
| 2017/0000180 A1 | 1/2017 | Arne et al. |
| 2018/0168490 A1* | 6/2018 | Jones ..................... A61B 1/041 |

* cited by examiner

SAMPLING DEVICE FOR DRUG DEVELOPMENT AND DIAGNOSIS OF GASTRIC-INTESTINAL DISEASES

CROSS-REFERENCE TO RELATED APPLICATIONS

This application is a 371 U.S. National Phase of International Application No. PCT/US2019/012073, filed Jan. 2, 2019, which claims the benefit of U.S. Provisional Application No. 62/612,834 filed on Jan. 2, 2018. The entire disclosures of the above applications are incorporated herein by reference.

GOVERNMENT CLAUSE

This invention was made with government support under Grant No. HHSF223201510146C awarded by the Food and Drug Administration (FDA). The Government has certain rights in this invention.

FIELD

The present disclosure relates generally to ingestible electronic devices and, more particularly, to an ingestible electronic device for collecting samples along the gastric-intestinal tract for use in, among other things, oral drug product design and the optimization and diagnosis of gastro-intestinal diseases.

BACKGROUND

Ingestible electronic capsules are centimeter-sized mechatronic devices designed to perform medical tasks by entering the gastric-intestinal tract. Such ingestible electronic devices have become more prevalent in recent years for use in the diagnosis and treatment of various ailments. One example of a conventional ingestible electronic device is an ingestible camera capable of capturing images from inside a living organism. However, images are frequently insufficient to diagnose or treat certain conditions, particularly conditions specific to the digestive or gastric-intestinal ("GI") tract, such as Small Intestine Bacterial Overgrowth ("SIBO"), Crohn's disease, Irritable Bowel Syndrome, and *H pylori* infection. In many instances, gastric-intestinal fluids are necessary to diagnose these conditions and complicated and invasive procedures may be necessary to obtain the gastric-intestinal fluids. Accordingly, it would be desirable to develop non-invasive sampling means that improve the diagnosis of certain digestive diseases, improve the development and evaluation of oral drugs and bioequivalences, and the understanding of gastric-intestinal microbiota.

The information provided in this section is for the purpose of generally presenting the context of the disclosure. Work of the presently named inventors, to the extent it is described in this section, as well as aspects of the description that may not otherwise qualify as prior art at the time of filing, are neither expressly nor impliedly admitted as prior art against the present disclosure.

SUMMARY

In various aspects, the present disclosure provides an ingestible electronic device for collecting samples along a gastric-intestinal tract. The ingestible electronic device includes a housing and a cap that connects to the housing and has a surface that defines a sampling port. The ingestible electronic device further includes a rotatable shaft that is disposed within the housing and that is configured to rotate the cap axially about the rotatable shaft and a motor that is connected to the rotatable shaft within the housing that is configured to axially rotate the rotatable shaft. The ingestible electronic device further includes one or more sample collection chambers within the housing that are configured to collect the gastric-intestinal samples and a microcontroller that is configured to control the motor and rotatable shaft so as to selectively align the sampling port of the cap with at least one of the sample collection chambers. Aligning the sampling port and the at least one sample collection chamber exposes the at least one sample collection chamber to the gastric-intestinal tract for the collection of one or more gastric-intestinal fluid samples.

In one aspect, each sample collection chamber includes one or more deformable cartridges.

In one aspect, at least one of the deformable cartridges includes foam material having a porosity ranging from greater than or equal to about 30% to less than or equal to about 90%. In various instances, the foam material is configured to enhance capillary forces or to provide additional filtration. For example, the foam material has an average pore diameter ranging from greater than or equal to about 50 nm to less than or equal to about 500 μm and controlling the average pore diameter prevents certain drug products and select intestinal content from entering the deformable cartridges.

In one aspect, each sample collection chamber of the one or more sample collection chambers comprises a first end, a second end, and sidewalls connecting the first end and the second end.

In one aspect, at least one sample collection chamber of the one or more sample collection chambers retains a time-correlated profile of the one or more gastric-intestinal fluid samples between the first end and the second end.

In one aspect, the first end is configured for exposure to the gastric-intestinal tract for sample collection and the second end and sidewalls are covered by a sealing coating.

In one aspect, the sealing coating comprises an impervious polymer, such as a rubber.

In one aspect, the interior surfaces of one or more of the cap and the housing are coated with a silicon-based grease.

In one aspect, the rotatable shaft comprises a protrusion that is configured to deform one or more of the one or more sample collection chambers so as to induce a negative vacuum effect with regard to the one or more sample collection chambers to facilitate gastric-intestinal fluid sample collection.

In one aspect, the ingestible electronic device further comprises one or more sensors that are operatively connected to the microcontroller. The one or more sensors are configured to obtain at least one of a temperature of the gastric-intestinal tract in the vicinity of the ingestible electronic device, a pH of the gastric-intestinal tract in the vicinity of the ingestible electronic device, a pressure of the gastric-intestinal tract in the vicinity of the ingestible electronic device, a specific force for of the ingestible electronic device, and an angular rate of the ingestible electronic device.

In one aspect, the microcontroller includes a transceiver configured to obtain a signal instructing the ingestible electronic device to perform gastric-intestinal fluid sample collection.

In one aspect, the ingestible electronic device has a diameter of greater than or equal to about 10 mm to less than or equal to about 14 mm and a length of greater than or equal to about 25 mm to less than or equal to about 30 mm.

In one aspect, the ingestible electronic device is less than about 10 grams in weight.

In one aspect, the ingestible electronic device includes first and second distal ends and at least one of the first and second distal ends is curved to improve transit through the gastric-intestinal tract.

In one aspect, the ingestible electronic device further includes one or more batteries. The one or more batteries provides an operational time of not less than about 40 hours of deployment within the gastric-intestinal tract.

In various other aspects, the present disclosure provides a method of determining drug concentration and drug release in a gastric-intestinal tract. The method includes collecting a plurality of gastric-intestinal fluid samples using the ingestible electronic device from a plurality of locations along the gastric-intestinal tract, including at least one gastric-intestinal fluid sample from one or more of the stomach, duodenum, jejunum, ileum, and colon.

In one aspect, appropriate volumes are collected and recovered for oral drug product design, microbiome analysis, and disease diagnosis.

In one aspect, the appropriate volumes is greater than or equal to about 5 µL to less than or equal to about 500 µL.

In one aspect, the collected gastric-intestinal fluid sample is limited to at least one particular sample collection chamber without being present in one or more of the other sample collection chambers.

In one aspect, the method of determining drug concentration and drug release in a gastric-intestinal tract further includes extracting one or more of the plurality of gastric-intestinal fluid samples from the ingestible electronic device using one or more of the following extracting techniques: withdrawal by syringe, collection by centrifugation, and solvent extraction.

In one aspect, collecting the plurality of gastric-intestinal fluid samples includes deploying the ingestible sample device within the gastric-intestinal tract for greater than or equal to about 40 hours to less than or equal to about 100 hours.

In one aspect, the method of determining drug concentration and drug release in a gastric-intestinal tract further includes altering the curvature of at least one end of the ingestible electronic device to increase ease of swallowing and to improve rapid transit through the gastric-intestinal tract.

In various other aspects, the present disclosure provides an ingestible electronic capsule for the collection of samples along the gastric-intestinal tract. The ingestible electronic capsule includes a housing and a cap that is coupled to the housing to form an interior chamber. The cap includes a first surface and one or more first sidewalls extending therefrom. The housing includes a second surface and one or more second sidewalls extending therefrom. The first and second sidewalls interface to form the interior chamber and the first surface includes a sampling port. One or more sample collection chambers and a motor are disposed within the interior chamber formed by the housing and the cap. The motor is coupled to one of the cap and the one or more sample collection cambers so to align one of the one or more sample collection chambers and the sampling port of the cap so to allow for sample collection. The ingestible electronic capsule further includes a microcontroller that is also disposed within the interior chamber and that is in communication with at least the motor. The ingestible electronic capsule is configured to control the selective alignment of the sampling port and one of the one or more sample collect chambers and induce gastric-intestinal fluid sampling.

In one aspect, the second surface includes an access port.

In one aspect, the first surface and the one or more sidewalls of the cap defines an interior wall surface of the cap. The interior wall surface of the cap includes a protrusion extending therefrom and is coated with one or more sealing materials (such as, polyimide or a silicon-based grease).

In one aspect, each sample collection chamber of the one or more sample collection chambers includes a foam cartridge.

In one aspect, the motor is one of a step motor and a linear motor.

In one aspect, the motor is coupled to a rotatable shaft that couples the cap to the motor and the motor is configured to axially rotate the rotatable shaft.

In one aspect, the rotatable shaft includes a protrusion part extending therefrom that is configured to deform one or more of the one or more sample collection chambers so as to induce a negative vacuum effect with regard to the one or more sample collection chambers to facilitate gastric-intestinal fluid sample collection.

In one aspect, the microcontroller is disposed on a flexible printed circuit board.

In various other aspects, the present disclosure provides an ingestible electronic device for the collection of samples along the gastric-intestinal tract. The ingestible electronic device includes a housing having a first end that is coupled to a second end. The first end is rotatable around the second end. The first end includes a first surface and one or more first sidewalls extending therefrom. The first surface of the first end includes a sampling port. The second end includes a second surface and one or more second sidewalls extending therefrom. The second surface of the second end includes an access port. The first and second sidewalls interface to form an interior chamber. A plurality of foam cartridges are disposed within the interior chamber formed by the first and second sidewalls. A motor and a microcontroller are also disposed within the interior chamber. The motor is coupled to the first end of the housing and is configured to axially rotate the first end of the housing so to align one foam cartridge of the plurality of foam cartridges and the sampling port of the first end to collect gastric-intestinal fluid by the selected foam cartridge. The microcontroller is in communication with at least the motor and is configured to control the selective alignment of the sampling port and one foam cartridge of the plurality of foam cartridges so to induce the gastric-intestinal fluid sampling.

This section provides a general summary of the disclosure and is not a comprehensive disclosure of its full scope or all of its features. Further areas of applicability of the present disclosure will become apparent from the detailed description, the claims, and the drawings. However, the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

In the drawings, reference numbers may be reused to identify similar and/or identical elements.

DETAILED DESCRIPTION

Among other features, the present disclosure provides an autonomous wireless sampling device in the form of an ingestible electronic capsule or pill for fluid collection within the gastric-intestinal tract allowing, inter alia, in vivo drug dissolution monitoring to aid the design of oral medications and treatments and generic drug products and location specific microbiota analysis. The sampling device may collect multiple specimens or samples of gastric-intestinal tract fluid and store these samples in isolated chambers or cartridges. After the ingestible electronic pill is expelled and cleaned, the collected samples may be extracted from the chambers for analysis. The locations where the one or more samples were collected may be determined using x-rays or time-based estimations. Further, wireless communication between the sampling device and an external unit may allow remote triggering of the sampling action as well as constant monitoring of the ingestible electronic device during deployment. In various instances, the sampling device may obtain specimens from one or more of the stomach, duodenum, jejunum, ileum, colon, and combinations thereof.

Figure 1:
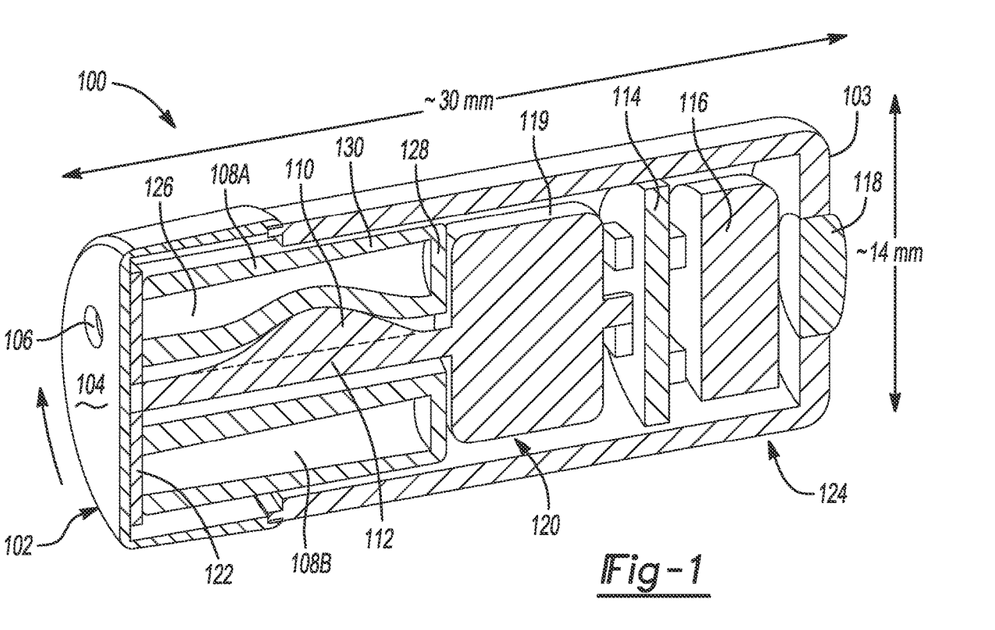
FIG. 1 is a cross-sectional perspective view of an example ingestible electronic capsule according to certain aspects of the present disclosure.

An exemplary and schematic illustration of an example ingestible electronic device or capsule 100 is shown in FIG. 1. The sampling device 100 is designed to be ingested by the subject (i.e., human or animal) and passed through the subject's gastric-intestinal tract before being expelled as waste. For example, in certain instances, the sampling device 100 has a length of greater than or equal to about 25 mm to less than or equal to about 30 mm and a width or diameter of greater than or equal to about 10 mm to less than or equal to about 14 mm. In certain instances, the diameter of the sampling device 100 may vary along the length of the sampling device 100. For example, a first end 104 of the sampling device 100 may have a first diameter that is less than or greater than a second diameter of a second end 103 of the sampling device 100. The (emptied) sampling device 100 may weigh greater than or equal to about 5 grams to less than or equal to about 15 grams.

The sampling device 100 includes a cap 102 and a housing element 124 connected thereto to form an interior chamber 119. The cap 102 includes a first end or surface 104 having a sampling port 106 formed therein. The first surface 104 of the cap 102 is parallel with a second end or surface 103 of the housing element 124. The second surface 103 of the housing element 124 includes an access port 118, which may be used to access components within the sampling device 100 for purposes of performing maintenance or the like (e.g., battery replacement).

One or more sample collection chambers (e.g., 108A and 108B) are disposed within the interior chamber 119 formed between the first end 104 and the second end 103. Although only two sample collection chambers 108 are shown in FIG. 1, according to some examples, eight or more sample collection chambers 108 may be included within the sampling device 100 without deviating from the teachings herein. Each sample collection chamber 108 includes a first end 126, a second end 128, and sidewalls 130 connecting the first and second ends 126, 128. The sample collection chambers 108 are configured to collect gastric-intestinal fluids from a subject's gastric-intestinal tract when the first end 126 of the sample collection chamber 108 is aligned with the sampling port 106 and exposed to the subject's gastric-intestinal tract. According to some examples, the one or more sample collection chambers 108 may collect one or more gastric-intestinal tract samples by virtue of a capillary force and/or suction force that draws the gastric-intestinal fluid samples into the sample collection chambers 108. In certain aspects, the one or more sample collection chamber 108 may each collect an amount of gastric-intestinal fluid ranging from about 5 μL to about 500 μL.

In certain aspects, the sample collection chambers 108 may be emptied prior to ingestion and sample collection. In other aspects (as seen for example in FIG. 2), each sample collection chamber 108 may include one or more foam-like cartridges 312 that absorb and retain the gastric-intestinal samples. In still other aspects, the sample collection chambers 108 may further include one or more sealing coating that coats one or more of the first end 126, the second end 128 and the sidewalls 130 of each sample collection chamber 108. For example, with specific reference to cartridge 108A, the second end 128 and sidewalls 130 may be coated with the sealing coating (not shown), while the first end 126 may remain coating-free to facilitate sample collection (e.g., when the sampling port 106 is aligned with the sample collection chamber 108a). The sealing coating may comprise an impervious polymer, such as rubber and may prevent cross contamination between samples within the adjacent sample collection chambers 108. In certain instances, a sealing layer 122 may also be disposed between the first ends 126 of the sample collection chambers 108 and the cap 102. The sealing layer 122 may be configured to prevent, for example, (i) unwanted ingress and egress of fluid (e.g., gastric-intestinal fluids) in and out of the sampling device 100 and (ii) cross contamination between the various sample collection chambers 108. The sealing layer 122 may be manufactured from any suitable material known in the art for accomplishing one or more of the foregoing objectives including, for example, plastic (e.g., polyimide) or grease (e.g., silicon grease).

With renewed reference to FIG. 1, the sampling device 100 includes a rotatable shaft 112 that connects the cap 102 to a motor 120. The rotatable shaft 112 and motor 120 may be configured to rotate the cap 102 axially about the rotatable shaft 112 so that the sampling port 106 aligns with one of the sample collection chambers 108. In certain aspects, the rotatable shaft 112 includes a protrusion 110 that is configured to deform (e.g., squeeze) one or more of the sample collection chambers 108 by applying a force to a sidewall of the sample collection chamber(s) 108 and thereby inducing a suction in the sample collection chamber(s) 108 when the force is withdrawn. More specifically, the deformation induced by the protrusion 110 may cause the sample collection chamber 108 exposed to the gastric-intestinal tract to draw one or more gastric-intestinal samples into the exposed sample collection chamber 108 by suction created when the applied force is withdrawn.

As the skilled artisan will recognized, in certain other aspects, the sampling device 100 may exclude a rotatable shaft 112 and the motor 120 may be coupled to the one or more sample collection chambers 108. In such instances, the motor 120 may be configured to rotate the one or more sample collection chambers 108 relative to the sampling port 106. As such, according to some examples, the motor 120 may include one of a miniature stepper motor, a linear motor, or the like.

Figure 6:
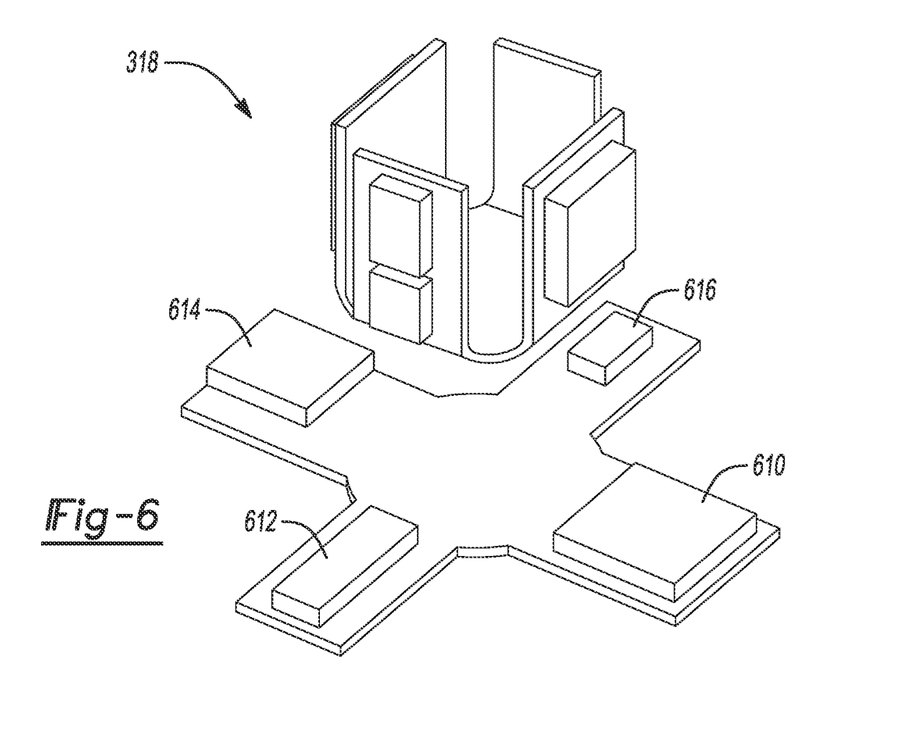
FIG. 6 is a perspective view of a flexible printed circuit board of the example ingestible electronic capsule of FIG. 2.

The sampling device 100 also includes a microcontroller 114 that is operatively connected (i.e., directly connected or connected via one or more intermediate components) to the motor 120. In some examples (for example, as seen in FIG. 6), the microcontroller 114 may be included on a circuit board (e.g., a PCB). The microcontroller 114 may include one or more processors (not shown) and memory (not shown) and is configured to control the motor 120. For example, according to some implementations, the microcontroller 114 may be configured to instruct the motor 120 to actuate so as to turn the rotatable shaft 112 and, consequently, the cap 102 by virtue of its connection to the rotatable shaft 112. In this manner, the microcontroller 114 may be configured to selectively align the sampling port 106 of the cap 102 with a given chamber (e.g., chamber 108a), thereby exposing the chamber (e.g., chamber 108a) to the gastric-intestinal tract for sample collection. The sample device 100 also include a battery 116 that is configured to supply power to the microcontroller 114 and/or motor 120. According to some examples, the battery 116 may provide an operational time of not less than about 40 hours of deployment within the gastric-intestinal tract.

Figure 2:
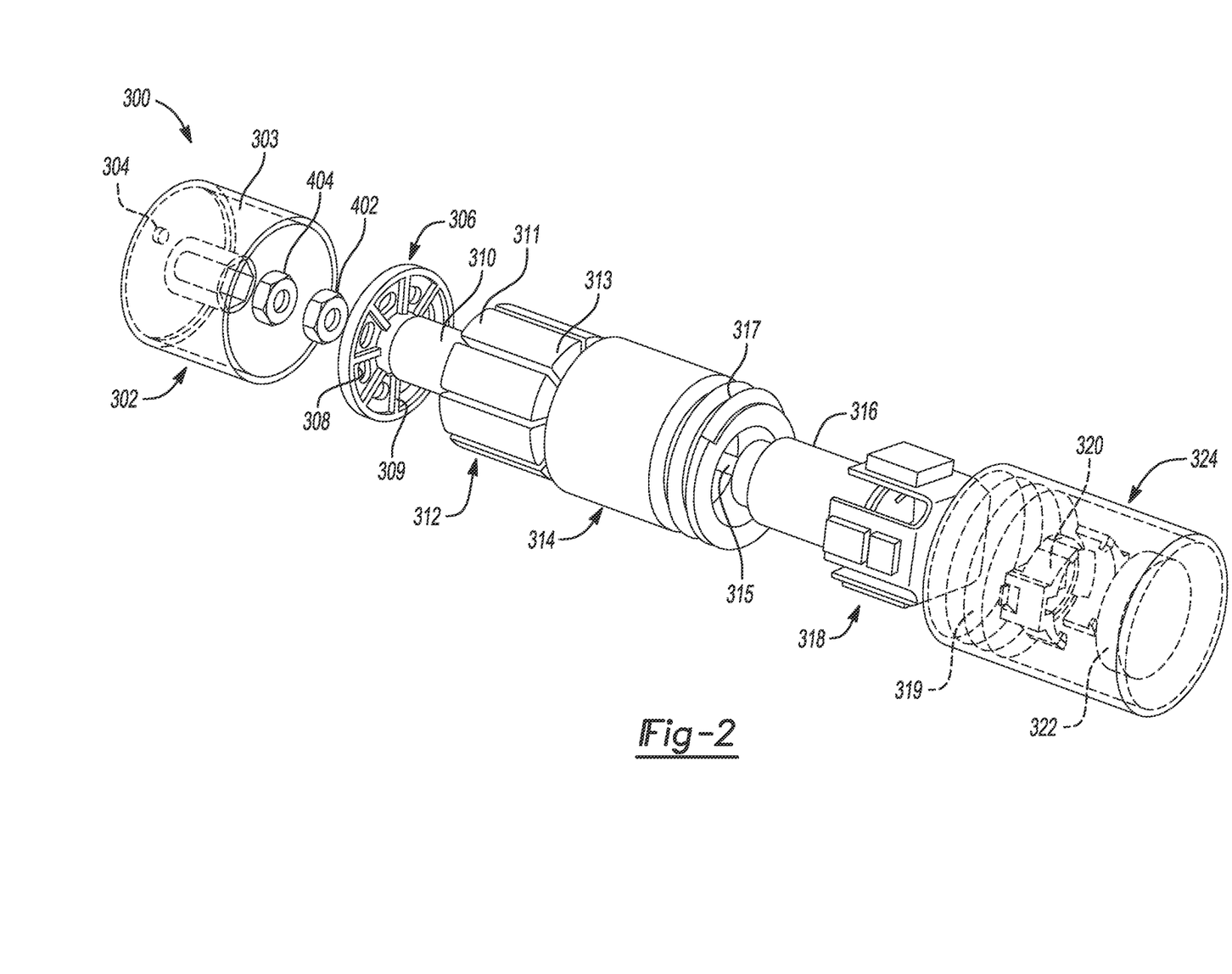
FIG. 2 is an exploded perspective view of an example ingestible electronic capsule according to certain aspects of the present disclosure.
Figure 3:
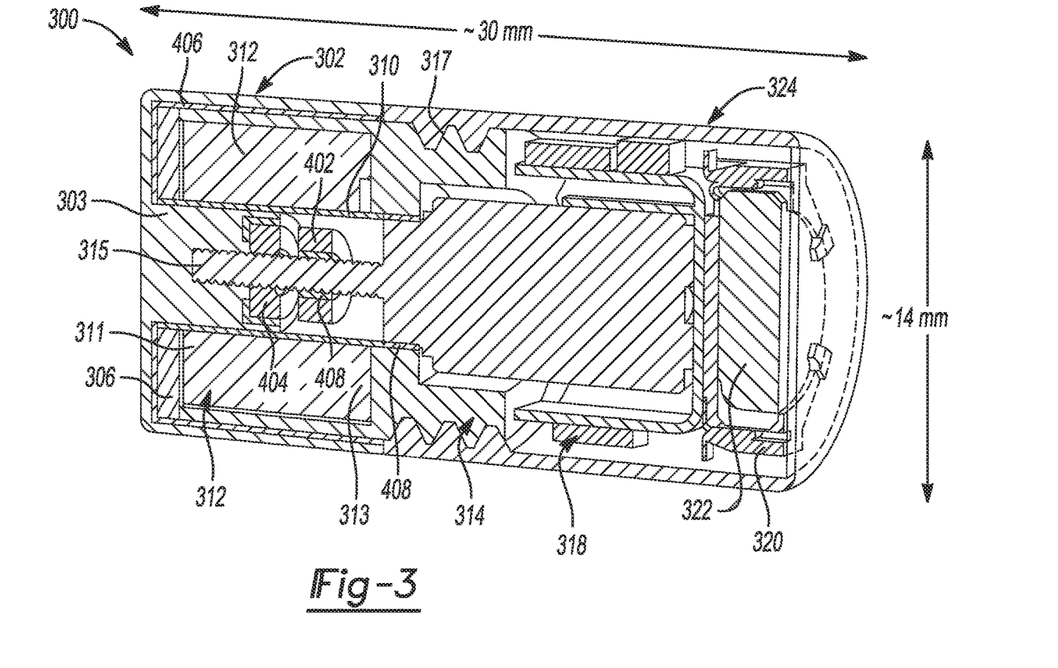
FIG. 3 is a cross-sectional perspective view of the example ingestible electronic capsule of FIG. 2.
Figure 4:
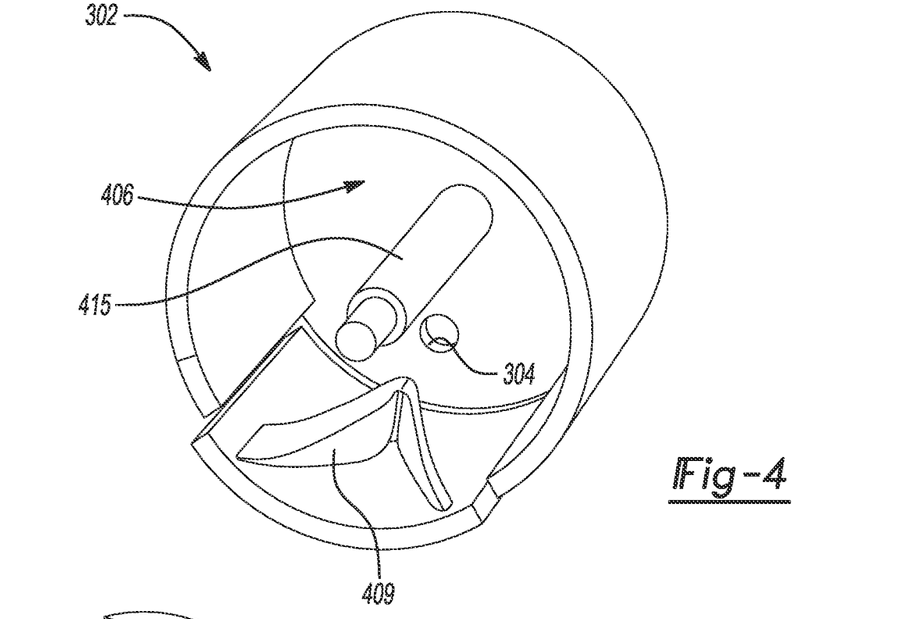
FIG. 4 is a perspective view of an example of a cap of the example ingestible electronic capsule of FIG. 2.

FIG. 2 is an exploded perspective view of another example of an ingestible electronic capsule or device 300, and FIG. 3 is a cross-sectional view of the example ingestible electronic capsule of FIG. 2. As in the prior example, the sampling device 300 includes a cap 302 and a housing element 324 that connects thereto. The cap 302 includes a first end or surface 303 having a sampling port 304 defined therewithin. Further, in certain instances, as seen in FIG. 4, an interior surface of the cap 302 may be coated with a sealing coating 406 and may further include a protrusion 409 having a screw-line shape that aids in the collection of the gastric-intestinal fluid sample and, subsequently, the expulsion of trapped air within the collected samples by adding occasional pressure to the sampling chamber or cartridge 312.

Figure 5A:
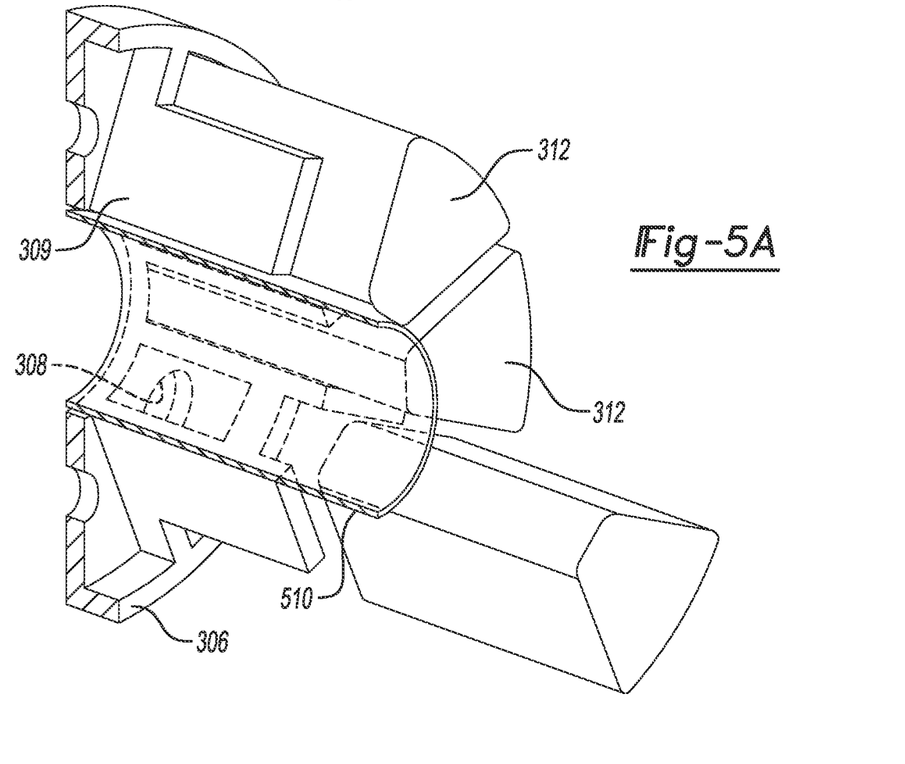
FIG. 5A is a perspective view of a front cartridge platform of the example ingestible electronic capsule of FIG. 2.
Figure 5B:
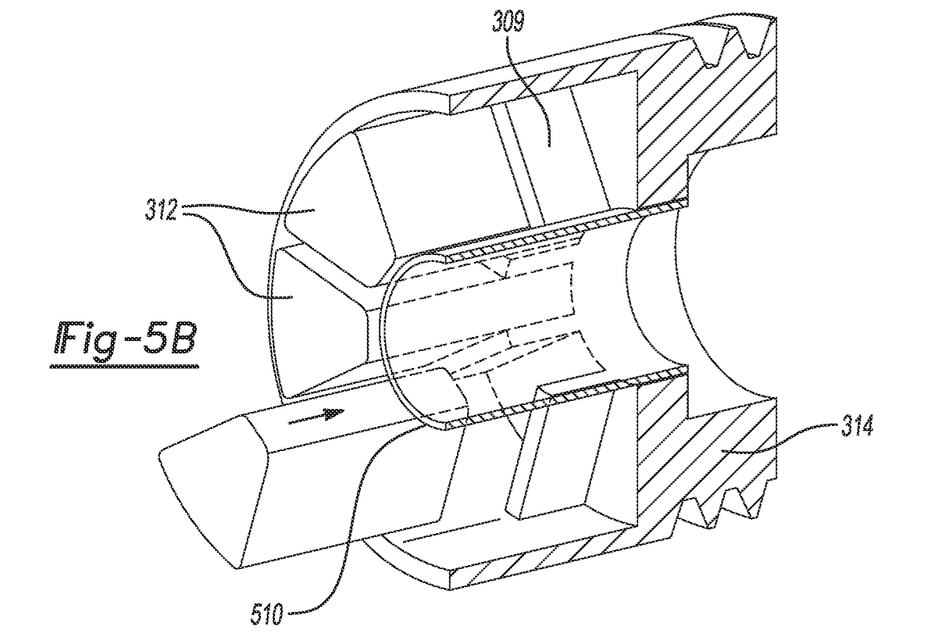
FIG. 5B is a perspective view of a back cartridge platform of the example ingestible electronic capsule of FIG. 2.

With renewed referenced to FIG. 2, the sampling device 300 further includes a front cartridge platform 306 that is disposed adjacent the first surface 303 of the front cap 302 as illustrated in FIG. 3. The front cartridge platform 306 includes a plurality of sampling inlets 308 and a plurality of fins 309, which separates the sampling inlets that form the plurality. The sampling inlets 308 of the front cartridge platform 306 and the sampling port 304 of the cap 302 are configured to create channels for the gastric-intestinal fluid samples to flow into one or more of the sample collection chambers or cartridges 312. As more clearly evidenced in FIGS. 5A and 5B, the front cartridge platform 306 and the back cartridge platform 314 (which described in further detail below) may help secure the foam cartridges that form the sample collection chambers 312 within discrete slots to help prevent inadvertent movement of the foam cartridges 312 when the cap 302 is rotated and to help reduce cross-contamination between the gastric-intestinal fluid samples collected by and stored in each foam cartridge 312. More particularly, as illustrated in FIGS. 5A and 5B, each foam cartridge 312 may be disposed within a particular channel or slot 510 as defined by the plurality of fins 309.

The foam cartridges 312 are configured to enhance capillary forces and/or aid filtration of particles within the gastric-intestinal fluid. For example, the foam cartridges 312 may each have a porosity ranging from greater than or equal to about 30% to less than or equal to about 90%, and in certain aspects, optionally greater than or equal to about 30% to less than or equal to about 70%. The pores may have an average diameter ranging from greater than or equal to about 50 nm to less than or equal to about 500 μm. The porosity of the foam cartridges 312 and the diameters of the pores can be varied for difference uses and environments. For example, in certain instances, each foam cartridge 312 may have regional porosity, such that a first portion of the foam cartridge 312 has a first porosity and a first average pore diameter, while a second portion of the foam cartridge 312 has a second porosity and a second average pore diameter. Likewise, each foam cartridge 312 forming the plurality may have a different porosity and/or average pore diameter. In certain aspects, the foam cartridges 312 may also be pretreated to enhance chemical stability or selectivity during the sampling period.

In this fashion, using fluid agitation principals, the transport and storage of the gastric-intestinal fluid samples from a first end 311 to a second end 313 of each foam cartridge 312 may facilitate the creation of a time-correlated profile of the sampled fluid within the foam cartridge 312. For example, gastric-intestinal fluid samples collected first may be stored towards the second end 313 of each foam cartridge 312, while subsequently collected gastric-intestinal fluid samples may be stored towards the first end 311 of each foam cartridge 312. Following expulsion and initial analyses (such as, the creation of a time-correlated profile), the gastric-intestinal fluid samples may be extracted from the foam cartridges 312 using, for example only, a direct withdrawal method, such as a by using a syringe, a centrifugation collection method, and/or a solvent extraction method.

Again with renew reference to FIG. 2, the sampling device 300 further includes a platform tube 310. The platform tube 310 connects the cap 302, the front cartridge platform 306, and the plurality of collection chambers 312 to the other components of the sampling device 300 including the back cartridge platform 314, the rotatable shaft 315, the motor 316, the microcontroller 318, the battery clamp 320, the battery 322, and the housing 324. As shown in further detail in FIG. 3, the platform tube 310 may house fastening elements (for example, one or more nuts 402, 404) that are configured to connect the cap 302 to the rotatable shaft, so to facilitate rotation of the cap 302 and thereby the sampling port 304.

The back cartridge platform 314 is configured to (i) house the platform tube 310 and the foam cartridges 312 and (ii) facilitate the alignment of the motor 316 and rotatable shaft 315 with the cap 302. For example, the back cartridge platform 314 may include grooves 317 that are complementary to the threads 319 of the device housing 324. The grooves 317 of the back cartridge platform 314 together with the grooves 319 of the device housing 324 may seal the sampling device 300 as seen in FIG. 3, so that the sampling port 304 serves as the only inlet and outlet for the sampling device 300.

Microcontroller 318 is a flexible or foldable printed circuit board ("PCB") and may be folded around the motor 316 so to conserve space within the sampling device 300. As illustrated in FIG. 6, in certain aspects, the printed circuit board 318 may include a monolithic microcontroller ("MCU") 610 with a built-in transceiver. In certain aspects, the printed circuit board 318 may further include a voltage booster 612, a motor driver 614, an antenna 616, and one or more other sensors (such as, an image sensor) (not shown). Using such a monolithic microcontroller simplifies the circuit design and reduces that area needed on the printed circuit board. However, as the skilled artisan will recognized in certain instances a monolithic microcontroller and a separate transceiver may be used as the microcontroller 318. Such a design may offer greater flexibility with regard to flash memory size and/or power consumption.

Figures 7A, 7B:
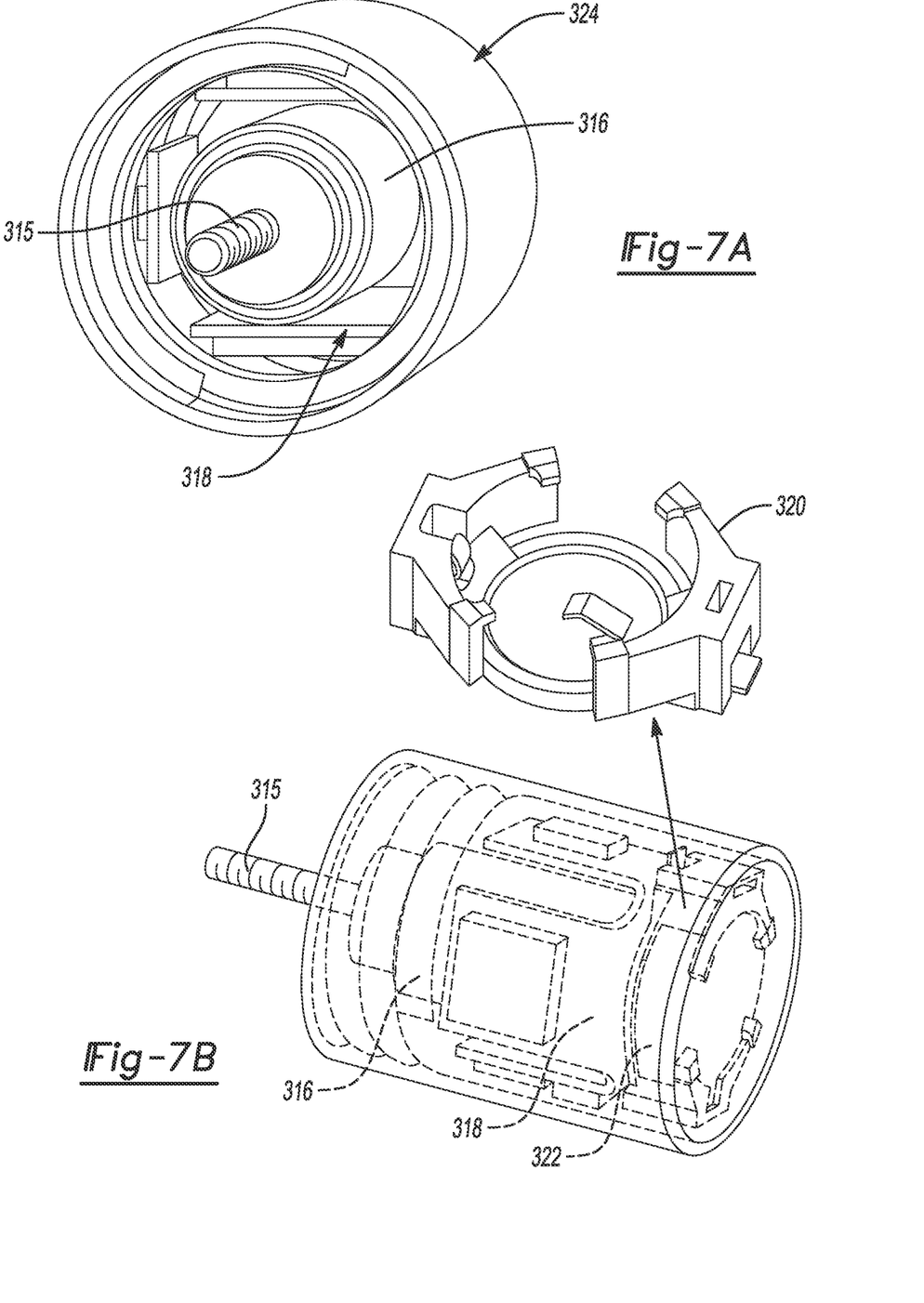
FIGS. 7A and 7B are perspective views of a housing of the example ingestible electronic capsule of FIG. 2.

Once again with renew reference to FIG. 2, as noted above, sampling device 300 includes a battery clamp 320 and a battery 322, which are disposed within the housing 324, as more clearly seen in FIGS. 7A and 7B. Although only a single clamp 320 and a single battery 322 are shown, the skilled artisan will appreciate that any suitable number of clamps 320 and/or batteries 322 may be utilized without deviating from the teachings herein. The battery clamp 320 is configured to secure the battery 322. However, in various instances, the battery clamp 320 and battery 322 may not be permanently fixed, so to allow removal and replacement of the battery 322.

As noted above, FIG. 3 is a cross-sectional view of the sampling device 300 of FIG. 2, in assembled form. More particularly, FIG. 3 more clearly illustrates the fastening elements 402, 404 housed within the platform tube 310. The fastening elements include a stopper nut 402 and a cap nut 404. The stopper nut 402 and a cap nut 404 are configured to connect the cap 302 to the rotatable shaft 315 of the motor 316. As shown, the stopper nut 402 is fixed upon the rotatable shaft 415 and the cap nut 404 is fixed within the cap 302. The pressure between the cap 302 and the front cartridge platform 306 may be adjusted by altering the position of the stopper nut 402 along the rotatable shaft. Those having ordinary skill in the art will appreciate that other suitable fastening elements may be employed in addition, or as alternatives to, the nuts 402, 404 without deviating from the teachings herein.

Furthermore, FIG. 3 more clearly illustrates the sealing elements 408 and sealing coatings 406 within the sampling device 300. More particularly, in some examples, sealing elements 408 are used to ensure that liquid does not enter the sampling device 300 except through the sampling port 304. For example, in some implementations, epoxy or the like may be included to seal the ingestible electronic device 300 and secure various components (e.g., the motor and/or fastening elements 402, 404) within the housing 324. In addition, in some implementations, a sealing coating 406 may be included between the cap 302 and the front cartridge platform 306 and the back cartridge platform 314. The sealing coating 406 may include a grease, such as a synthetic grease or a silicone-based grease.

Figure 8:
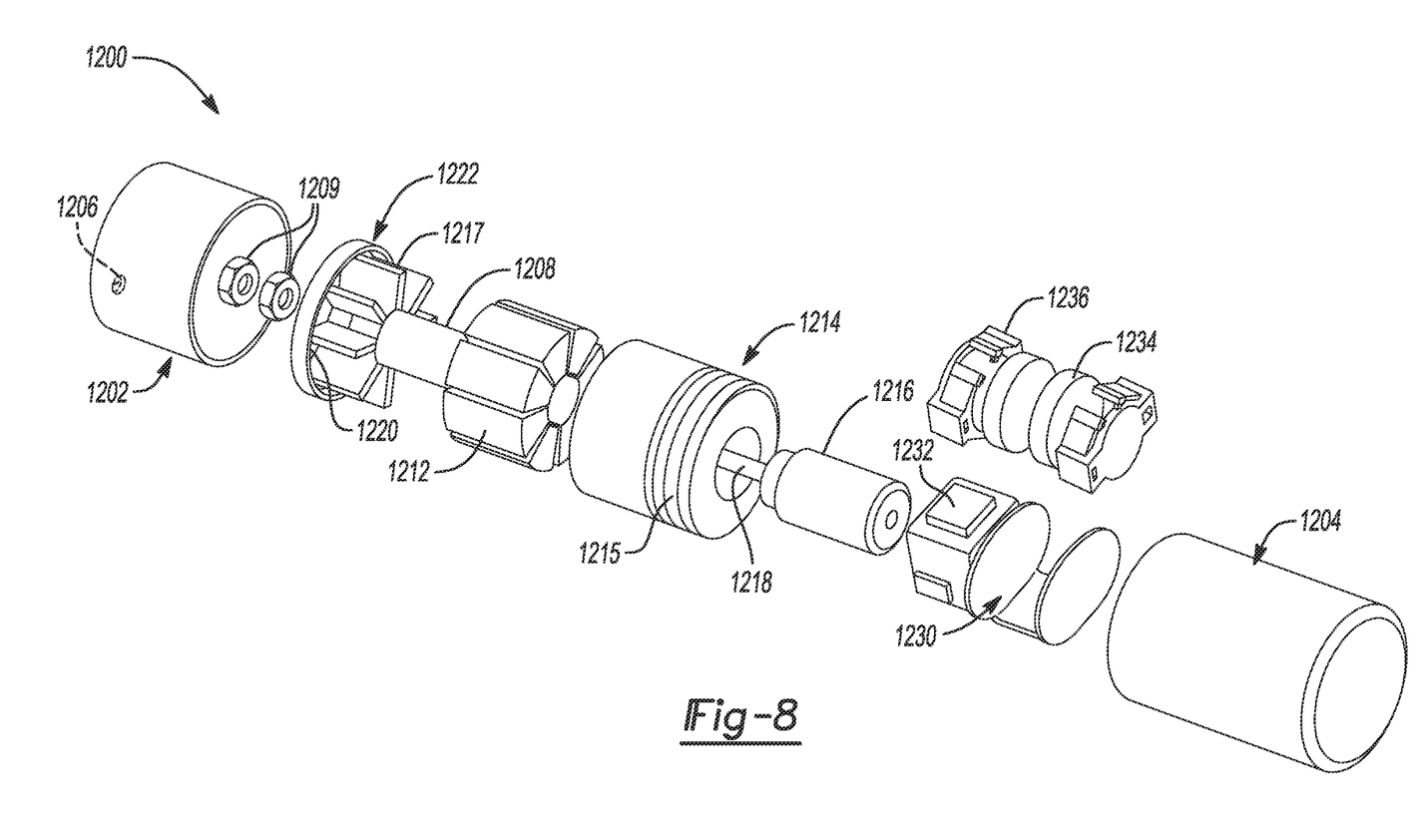
FIG. 8 is an exploded perspective view of another example of an ingestible electronic capsule according to certain aspects of the present disclosure.
Figure 9:
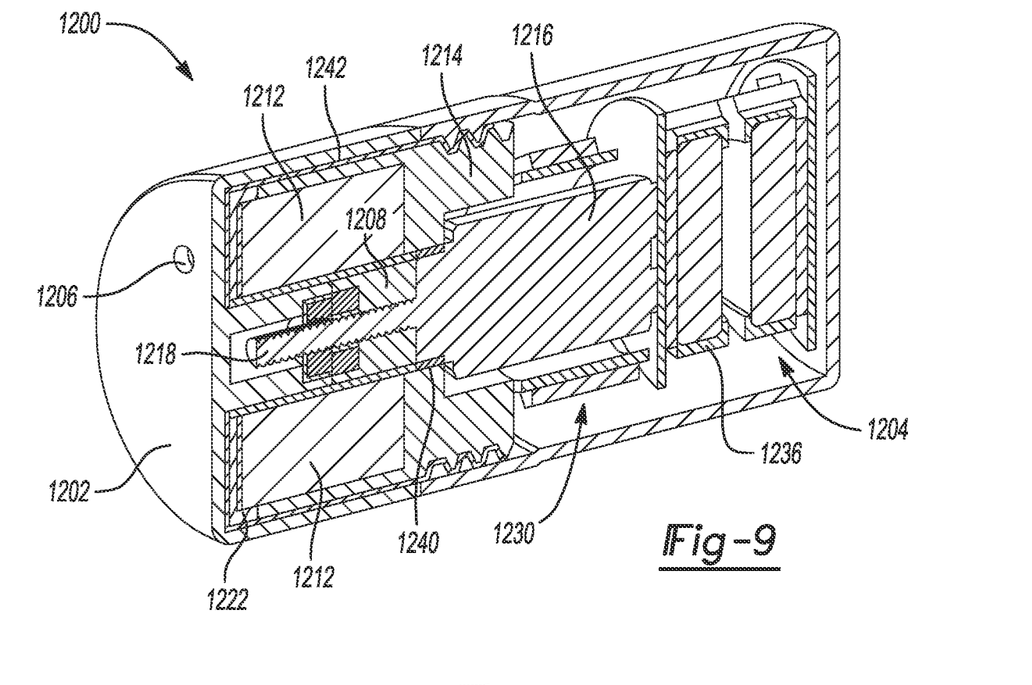
FIG. 9 is cross-sectional perspective view of the example ingestible electronic capsule of FIG. 8.

FIG. 8 is an exploded perspective view of another example of an ingestible electronic capsule or device 1200, and FIG. 9 is a cross-sectional view of the example ingestible electronic capsule 1200 of FIG. 8. As in the prior examples, the sampling device 1200 includes a cap 1202 having a sampling port 1206 formed therein and a housing element 1204 that connects thereto. The sampling device 1200 as in the prior examples also includes a platform tube 1208 comprising one or more fasteners 1209; a plurality of foam cartridges that form the sample collection chambers 1212; and a back cartridge platform 1214 that includes a plurality of grooves 1215 and is configured to (i) house the platform tube 1208 and the foam cartridges 1212 and (ii) facilitate the alignment of a motor 1216 and rotatable shaft 1218 with the cap 1202.

The sampling device 1200 also includes a front cartridge platform 1222 that includes a plurality of sampling inlets 1220 formed therein. However, the sampling device 1200 illustrated in FIGS. 8 and 9 has a plurality of fins 1217 having a length that is greater than that seen in FIGS. 2 and 3 so to aid in the placement of the foam cartridges 1212 disposed therebetween. In each instances, the fins 309, 1217 may have a length ranging from greater than or equal to about 20% to less than or equal to about 90% of the length of the foam cartridges 312, 1212.

Figure 10:
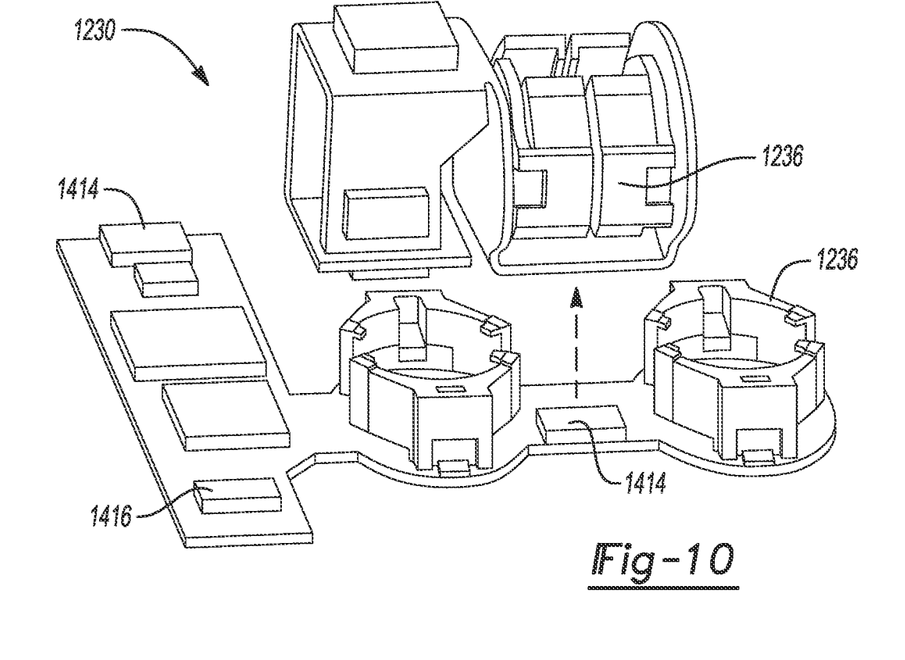
FIG. 10 is a perspective view a flexible printed circuit board of the example ingestible electronic capsule of FIG. 8.

With renewed reference to FIG. 8, the sampling device 1200 also includes a microcontroller 1232 formed on a flexible printed circuit board 1230. However, the flexible printed circuit board 1230 as more clearly illustrated by FIG. 10 is further configured to receive a plurality of batteries 1234 and a plurality of battery clamps 1236. As shown in FIG. 10, in various instances, the flexible printed circuit board 1230 (similar to the printed circuit board 318 illustrated in FIG. 6) may further include a voltage booster 1412, a motor driver 1414, an antenna 1416, and one or more other sensors (such as, an image sensor) (not shown).

As noted above, FIG. 9 is a cross-sectional view of the sampling device 1200 of FIG. 8. As in the instance of FIGS. 2 and 3, FIG. 9 more clearly illustrates certain components of the sampling device 1200. More particularly, FIG. 9 more clearly illustrates the sealing elements 1240 that are used to ensure that liquid does not enter the sampling device 1200 except through the sampling port 1206 and the sealing coating 1242 that is disposed between the cap 1202 and the front cartridge platform 1222 and the back cartridge platform 1214.

Figure 11:
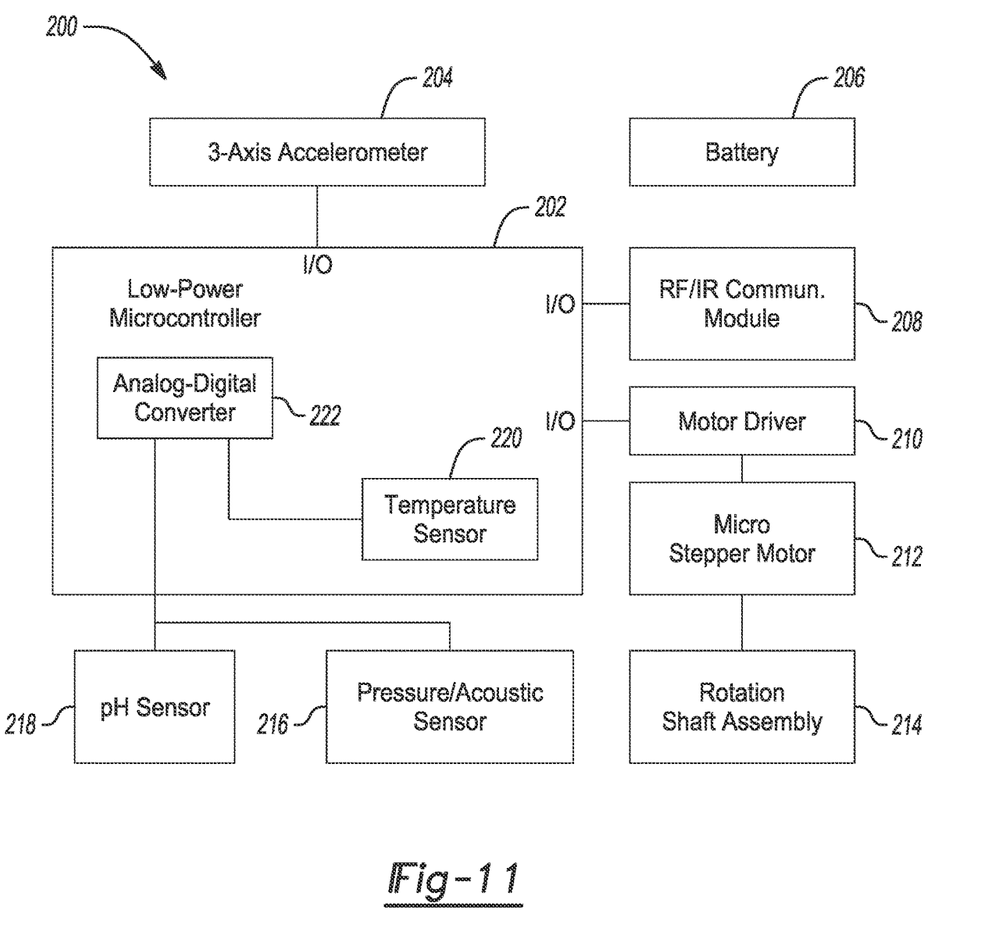
FIG. 11 is a functional block diagram of an example ingestible electronic capsule according to certain aspects of the present disclosure.

FIG. 11 is a functional block diagram of an example ingestible electronic capsule 200. For example, as in the instances of FIGS. 1, 2, and 8, the sampling device 200 may include a microcontroller 202 operatively connected to variety of other components via one or more input and/or output interfaces and a battery 206. For example, the sampling device 200 may include an additional sensor 204 (e.g., CMOS imager (not shown)) operatively connected to the microcontroller 202 via a first I/O interface (e.g., a port). The additional sensor 204 may be configured to sense the surrounding environment (e.g., by capturing photographic or video images) of the sampling device 200 as it passes along the gastric-intestinal tract.

In addition, the sampling device 200 may include a communication module 208 operatively connected to the microcontroller 202. In one example, the communication module 208 may communicate using a radio-frequency communications protocol. In another example, the communication module 208 may communicate using an infrared communications protocol. Regardless of the protocol employed, the communication module 208 may transmit and receive data wirelessly. In one example, the communication module 208 may be configured to obtain a signal instructing the sampling device 200 to collect one or more gastric-intestinal fluid samples. In such an example, the instruction may be passed along to the microcontroller 202, which may then issue a command causing a motor (e.g., motor 212) to rotate a rotatable shaft (e.g., rotatable shaft 214), which in turn rotates a sampling port into alignment with a particular chamber, which may be used to collect the gastric-intestinal fluid sample. In other examples, the communication module 208 may be configured to receive requests for information (e.g., sensor readings) and transmit responses to those requests. In other examples, the communication module 208 may transmit information (e.g., sensor readings, diagnostic information such as battery life, etc.) unprompted to an external device (e.g., a computer). Although shown as separate from the microcontroller 202, according to some examples, the communication module 208 may be embedded within the microcontroller 202.

In some examples, the sampling device 200 may include a motor driver 210, motor 212 (e.g., micro stepper motor), and rotation shaft assembly 214. The motor driver 210, motor 212, and rotation shaft assembly 214 may collectively be used to rotate a cap and, in turn, rotate a sampling port defined within the cap into alignment with a particular chamber to achieve gastric-intestinal fluid sampling. Further, in some implementations, the sampling device 200 may include one or more additional sensors. The one or more additional sensors are operatively connected to the microcontroller 202 and may include a pH sensor 218, a temperature sensor 220, and/or a pressure or acoustic sensor 216. In certain aspects, the microcontroller 202 may also include an analog-to-digital converter 222 to, for example, convert analog sensor measurements into digital sensor measurements.

While the temperature sensor 220 is shown as part of the microcontroller 202, according to some examples, the temperature sensor 220 may be external to the microcontroller 202 and connected to the microcontroller 202 via any suitable communication channel. Similarly, although shown as separate from the microcontroller 202, in some examples, the one or more additional sensors may be embedded within the microcontroller 202. The pH sensor 218 may be configured to obtain pH measurements within the gastric-intestinal tract in the vicinity of the sampling device 200. The pressure sensor 216 may be configured to obtain pressure measurements within the gastric-intestinal tract in the vicinity of the sampling device 200. Similarly, the temperature sensor 220 may be configured to obtain temperature measurements of the GI tract in the vicinity of the sampling device 200.

The components of the various sampling devices device (e.g., 100, 200, 300, and 1200) may be manufactured by stereolithography ("SLA") three-dimensional printing techniques. In other examples, one or more of the various components may be manufactured according to fused deposition modeling ("FDM") three-dimensional printing techniques. Of course, those having ordinary skill in the art will recognize that other suitable manufacturing techniques may be employed without deviating from the teachings of the instant disclosure.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

What is claimed is:

1. An ingestible electronic device for collecting samples along a gastric-intestinal tract, the ingestible electronic device comprising:
a housing;
a cap connected to the housing and comprising a surface defining a sampling port;
one or more sample collection chambers within the housing and configured to collect the gastric-intestinal samples, where at least one of the one or more sample collection chambers includes a wall which is mechanically deformable responsive to an applied force and includes a cartridge having a porous external surface that draws a sample into the chamber;
a rotatable shaft disposed within the housing and is configured to rotate one of the cap or the one or more sample collection chambers;
a motor connected to the rotatable shaft within the housing and configured to axially rotate the rotatable shaft; and
a microcontroller configured to control the motor and rotatable shaft so as to selectively align the sampling port of the cap with at least one of the sample collection chambers, thereby exposing the at least one sample collection chamber to the gastric-intestinal tract for collection of one or more gastric-intestinal fluid samples.

2. The ingestible electronic device of claim 1, wherein the cartridge is a foam material.

3. The ingestible electronic device of claim 2, wherein the cartridge comprises foam material having a porosity ranging from greater than or equal to about 30% to less than or equal to about 90%.

4. The ingestible electronic device of claim 3, wherein the foam material is chemically pretreated to enhance at least one of the chemical stability of the gastric-intestinal fluid sample and affinity of the sample collection chamber during the sampling period and during the sample extraction process.

5. The ingestible electronic device of claim 2 wherein the cartridge comprises foam material has an average pore diameter ranging from greater than or equal to about 50 μm to less than or equal to about 500 μm and by controlling the average pore diameters particles from drug products and select intestinal content are prevented from entering the deformable cartridges.

6. The ingestible electronic device of claim 1, wherein each sample collection chamber of the one or more sample collection chambers comprises a first end, a second end, and sidewalls connecting the first end and the second end.

7. The ingestible electronic device of claim 6, wherein at least one sample collection chamber of the one or more sample collection chambers retains a time-correlated profile of the one or more gastric-intestinal fluid samples between the first end and the second end.

8. The ingestible electronic device of claim 6, wherein the first end is configured for exposure to the gastric-intestinal tract for sample collection and the second end and sidewalls are covered by a sealing coating.

9. The ingestible electronic device of claim 8, wherein the sealing coating comprises an impervious polymer.

10. The ingestible electronic device of claim 1, wherein interior surfaces of one or more of the cap and the housing are coated with a silicon-based grease.

11. The ingestible electronic device of claim 1, wherein the rotatable shaft comprises a protrusion that is configured to provide the applied force, and the wall of the at least one sample collection chamber is mechanically deformable responsive to the applied force and provides suction to draw the sample into the chamber when the force is removed.

12. The ingestible electronic device of claim 1, further comprising one or more sensors operatively connected to the microcontroller, wherein the one or more sensors are configured to obtain at least one of a temperature of the gastric-intestinal tract in the vicinity of the ingestible electronic device, a pH of the gastric-intestinal tract in the vicinity of the ingestible electronic device, a pressure of the gastric-intestinal tract in the vicinity of the ingestible electronic device, a specific force of the ingestible electronic device, and an angular rate of the ingestible electronic device.

13. The ingestible electronic device of claim 1, wherein the microcontroller comprises a transceiver configured to obtain a signal instructing the ingestible electronic device to perform gastric-intestinal fluid sample collection.

14. The ingestible electronic device of claim 1, wherein the ingestible electronic device has a diameter of greater than or equal to about 10 mm to less than or equal to about 14 mm and a length of greater than or equal to about 25 mm to less than or equal to about 30 mm.

15. The ingestible electronic device of claim 1, wherein the ingestible electronic device is less than about 10 grams in weight.

16. The ingestible electronic device of claim 1, wherein the ingestible electronic device has a length of greater than or equal to about 25 mm to less than or equal to about 30 mm and a variable diameter along the length.

17. The ingestible electronic device of claim 1, wherein the ingestible electronic device comprises first and second distal ends and at least one of the first and second distal ends is curved to improve transit through the gastric-intestinal tract.

18. An ingestible electronic device for collecting samples along a gastric-intestinal tract, the ingestible electronic device comprising:
　a housing;
　a cap connected to the housing and comprising a surface defining a sampling port;
　one or more sample collection chambers within the housing and configured to collect the gastric-intestinal samples, wherein each sample collection chamber of the one or more sample collection chambers includes a first end, a second end, and sidewalls connecting the first end and the second end, such that the first end is configured for exposure to the gastric-intestinal tract for sample collection, and portions of the side walls are mechanically deformable responsive to an applied force;
　a cartridge disposed in at least one of the one or more sample collection chambers, where the cartridge has a porous external surface that draws a sample into the chamber;
　a rotatable shaft disposed within the housing;
　a motor connected to the rotatable shaft within the housing and configured to axially rotate the rotatable shaft; and
　a microcontroller configured to control the motor and rotatable shaft so as to selectively align the sampling port of the cap with at least one of the sample collection chambers, thereby exposing the at least one sample collection chamber to the gastric-intestinal tract for collection of one or more gastric-intestinal fluid samples.

\* \* \* \* \*

UNITED STATES PATENT AND TRADEMARK OFFICE
CERTIFICATE OF CORRECTION

| | |
|---|---|
| PATENT NO. | : 11,647,959 B2 |
| APPLICATION NO. | : 16/958165 |
| DATED | : May 16, 2023 |
| INVENTOR(S) | : Duxin Sun et al. |

It is certified that error appears in the above-identified patent and that said Letters Patent is hereby corrected as shown below:

In the Claims

At Column 14, Claim number 5, Line number 45, delete "µm" and insert --nm--.

Signed and Sealed this
Fourth Day of July, 2023

Katherine Kelly Vidal
*Director of the United States Patent and Trademark Office*